US00PP36010P2

(12) United States Plant Patent
de Jong

(10) Patent No.: US PP36,010 P2
(45) Date of Patent: Jul. 16, 2024

(54) ***SYMPHORICARPOS* PLANT NAMED 'KOLMAPINPOS'**

(50) Latin Name: ***Symphoricarpos* X *doorenbosii***
Varietal Denomination: Kolmapinpos

(71) Applicant: Kolster Holding B.V., Boskoop (NL)

(72) Inventor: Jan de Jong, Heelsum (NL)

(73) Assignee: KOLSTER HOLDING BV, Boskoop (NL)

( * ) Notice: Subject to any disclaimer, the term of this patent is extended or adjusted under 35 U.S.C. 154(b) by 0 days.

(21) Appl. No.: 18/497,920

(22) Filed: Oct. 30, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Symphoricarpos* plant named 'Kolmapinpos' that is characterized by its large berries that are light pink in color, its suitability for use as a garden plant and as a container plant, its dense growth habit with many lateral branches, and its straight lateral branches.

3 Drawing Sheets

Botanical classification: *Symphoricarpos* X *doorenbosii*.
Variety denomination: 'Kolmapinpos'.

BACKGROUND OF THE INVENTION

The present invention relates to a new and distinct cultivar of *Symphoricarpos* X *doorenbosii* that will be referred to hereafter by its cultivar name, 'Kolmapinpos'. The new cultivar represents a new cultivar of snowberry or coralberry that is used as a landscape and container plant.

The new Invention arose from an ongoing controlled breeding program in Heelsum, The Netherlands. The goal was to select a new unique cultivar of *Symphoricarpos* with pink colored berries.

The new cultivar arose from open pollination in August of 2010 of an unpatented proprietary plant in the Inventor's breeding program, designated as 09-016, as the female parent. The male parent is therefore unknown. 'Kolmapinpos' was selected as a single unique plant from amongst the resulting seedlings in October of 2013.

Asexual propagation of the new cultivar was first accomplished under the direction of the Inventor using softwood stem cuttings in November of 2013 in Boskoop, The Netherlands. Asexual propagation by softwood stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Kolmapinpos' as a new and unique cultivar of *Symphoricarpos*.

1. 'Kolmapinpos' exhibits large berries that are light pink in color.
2. 'Kolmapinpos' exhibits suitability for use as a garden plant and as a container plant.
3. 'Kolmapinpos' exhibits a dense growth habit with many lateral branches.
4. 'Kolmapinpos' exhibits straight lateral branches.

The female parent of 'Kolmapinpos' differs from 'Kolmapinpos' in having less berries per branch and shorter lateral branches. 'Kolmapinpos' can be most closely compared to the *Symphoricarpos* cultivars 'Kolmatemta' (not patented) and 'Kolmarufa' (not patented). 'Kolmatemta' and 'Kolmarufa' are both similar to 'Kolmapinpos' in having large pink berries and straight lateral branches. 'Kolmatemta' differs from 'Kolmapinpos' in having longer lateral branches with more compact clusters of berries and berries that are darker pink in color. 'Kolmarufa' differs from 'Kolmapinpos' in having longer lateral branches with more compact clusters of berries and berries that are initially darker pink in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Lawn and Garden Retailer, Greenhouse Product News, Bloomin' Easy Plants, Curoplant Company, and Van Belle Young Plants.

BRIEF DESCRIPTION OF THE DRAWINGS

The accompanying color photographs illustrate the overall appearance and distinct characteristics of the new *Symphoricarpos*. The photographs in FIG. 1 and FIG. 3 were taken a 1-year-old plant as grown outdoors in a 2-gallon container in Abbotsford, British Columbia, Canada and the photograph in FIG. 2 was taken of a 3-year-old plant as grown in a trial garden in Abbotsford, British Columbia, Canada.

The photograph in FIG. 1 provides a view of the plant habit of 'Kolmapinpos'.

Figure 1:
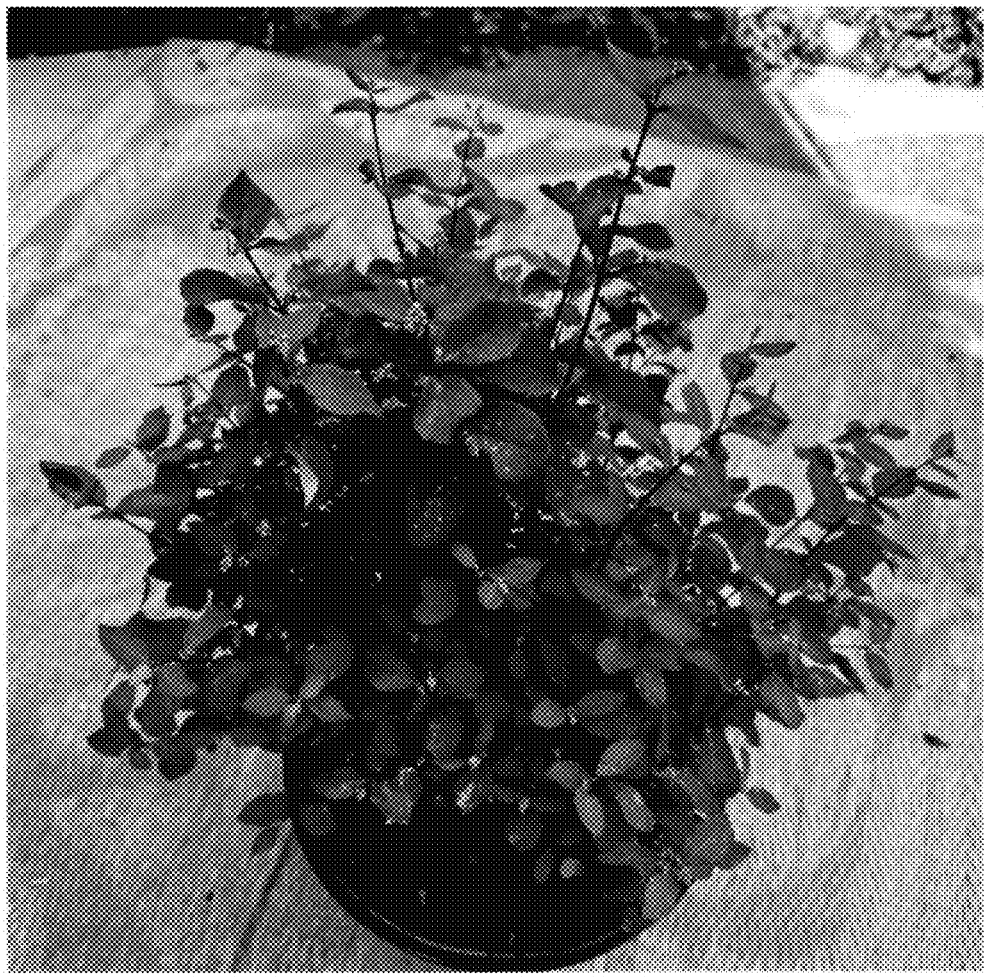
Figure 2:
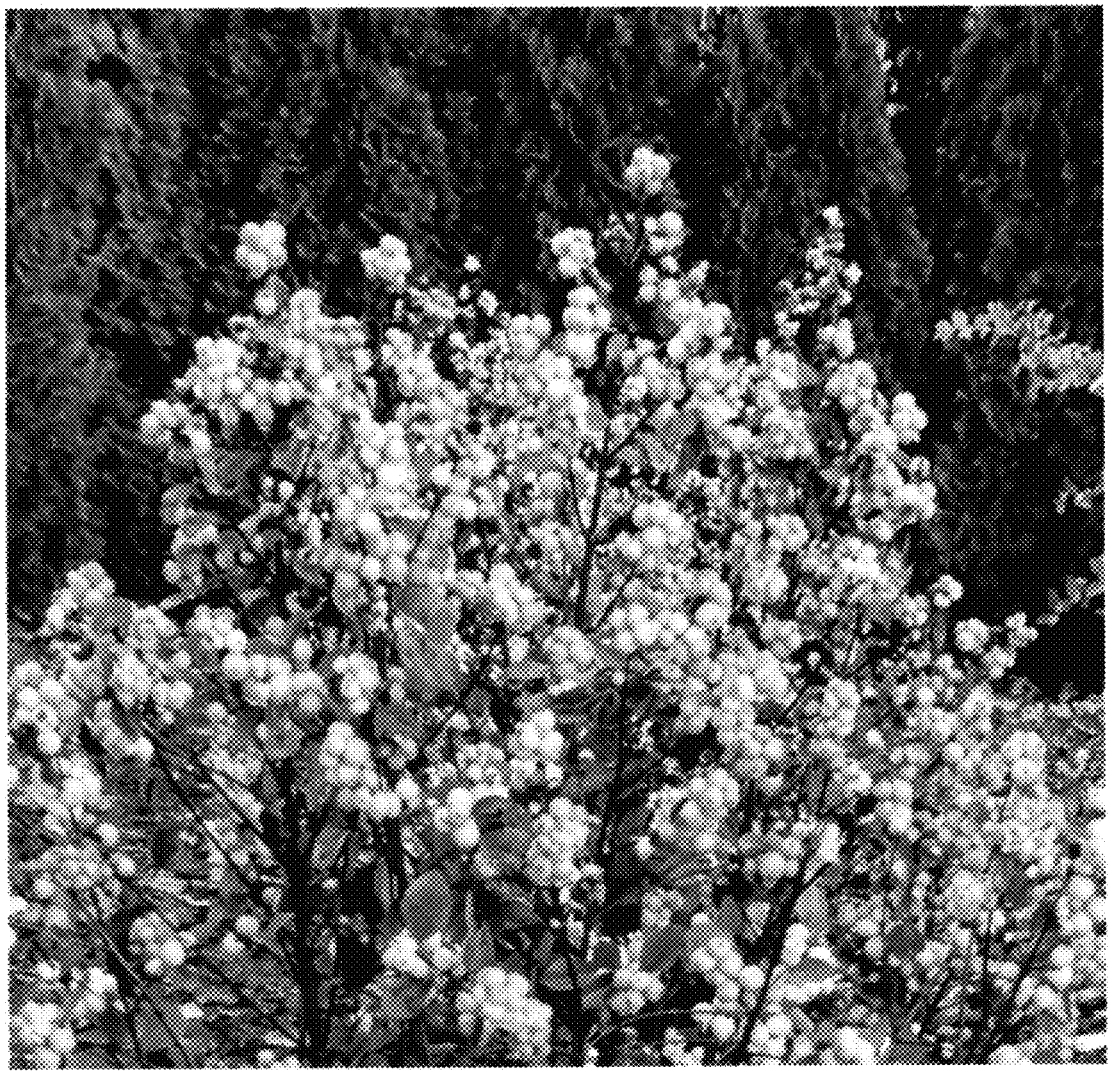

The photograph in FIG. 2 provides a view of the berries of 'Kolmapinpos'.

Figure 3:
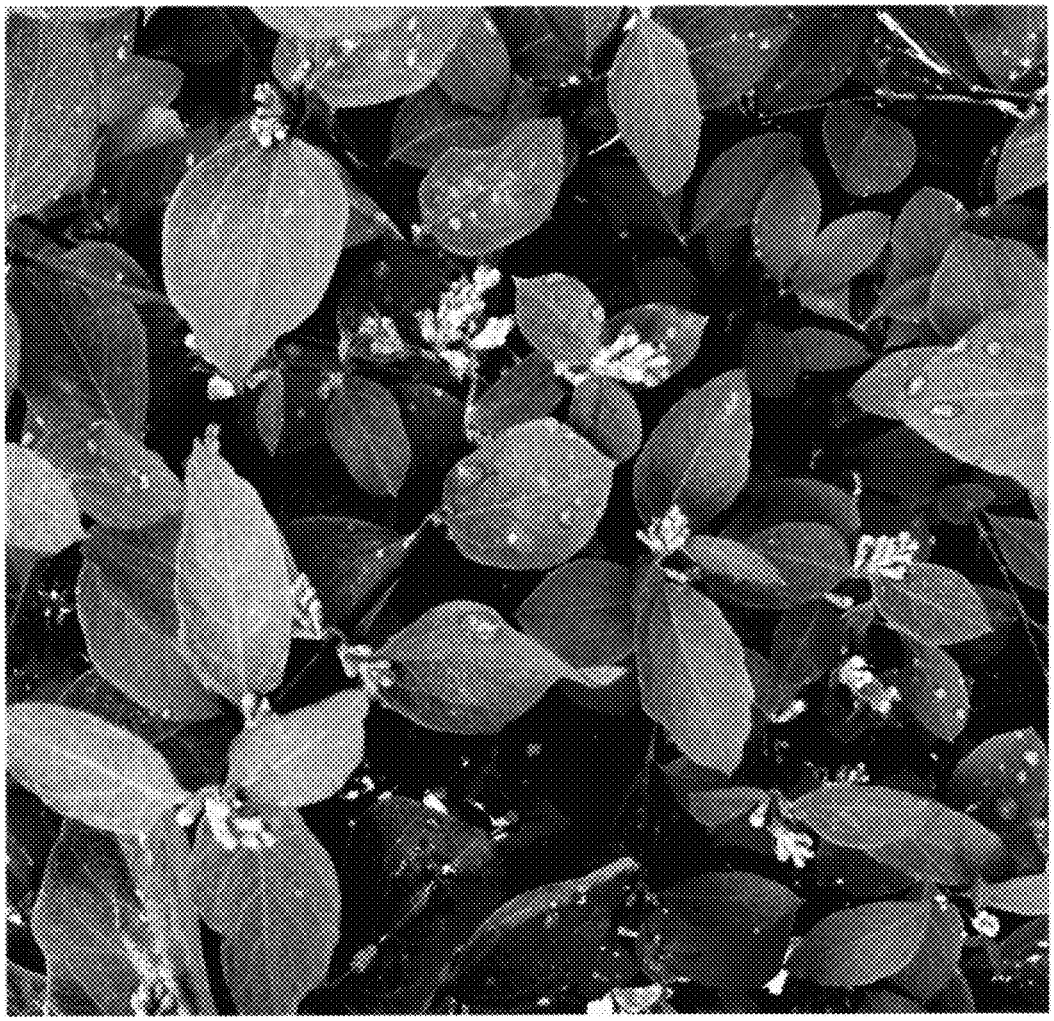

The photograph in FIG. 3 provides a view of the developing inflorescences of 'Kolmapinpos'.

The colors in the photographs may differ slightly from the color values cited in the detailed botanical description, which accurately describe the colors of the new *Symphoricarpos*.

DETAILED BOTANICAL DESCRIPTION

The following is a detailed description of 1-year-old plants of the new *Symphoricarpos* as grown outdoors in 2-gallon containers in Abbotsford, British Columbia, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June to July in The Netherlands.

*Plant habit*.—Upright spreading, densely branched with straight branches.

*Plant size*.—An average of 40 cm in height, 45 cm in width as a one-year-old plant in a 2-gallon container and 70 cm in height and 1 meter in spread as a 3-year-old plant in the landscape.

*Cold hardiness*.—At least to U.S.D.A. Zone 5.

*Diseases and pests*.—No susceptibility or resistance to diseases or pests has been observed.

*Root description*.—Fibrous, 199A in color.

*Propagation*.—Softwood stem cuttings.

*Root development*.—Roots initiate in about 6 weeks in June, 10 weeks in January and will fully root as young plant in about one year and two years to finish a young plant that produces berries.

*Growth rate*.—Moderately vigorous.

Branch description:

*Branch shape*.—Rounded.

*Stem color*.—New growth; 142A, mature wood; 197A and 196A.

*Branch size*.—Main branches; up to 24 cm in length and 1 cm in diameter, lateral branches; an average of 26 cm in length and 5 mm in diameter.

*Branch surface*.—New growth; glabrous and glossy, mature wood is dull and smooth and becoming bark-like as it ages.

*Branching*.—Average of 10 main branches, average of 16 lateral branches per main branch.

*Internode length*.—Average of 3 cm.

Foliage description:

*Leaf shape*.—Ovate to broadly ovate.

*Leaf division*.—Simple.

*Leaf base*.—Rounded to acute.

*Leaf apex*.—Acute to bluntly acute.

*Leaf fragrance*.—None.

*Leaf venation*.—Pinnate, inconspicuous, colors match leaf surface colors.

*Leaf margins*.—Entire.

*Leaf arrangement*.—Opposite to whorled.

*Leaf attachment*.—Petiolate.

*Leaf surface*.—Glabrous and matte on upper surface and lower surface.

*Leaf size*.—Average of 2.5 cm in length and 1.5 cm in width.

*Leaf quantity*.—Average of 20 pair per lateral branch.

*Leaf color*.—Young; upper surface 140A, lower surface 138B, mature; upper surface N134A, lower surface 138B.

*Petioles*.—3 mm in length and 1 mm in width, color; young 140A, mature 185A, surface; glabrous and matte.

*Stipules*.—None.

Flower description:

*Flower arrangement and shape*.—Single campanulate flowers arranged in terminal spikes or solitary in leaf axils.

*Flower aspect*.—Drooping.

*Fragrance*.—None detected.

*Flower longevity*.—Average of 5 days, not persistent.

*Fruit longevity*.—Average of 1 month.

*Flower buds*.—Average of 2 mm in length and 2 mm in diameter, oval in shape, matte surface, 142A to 142B in color.

*Inflorescence size*.—Average of 1.5 cm in length, 1 cm in diameter.

*Flowers*.—Average of 5 mm in length, 4 mm in diameter.

*Petals*.—5, arranged in a single whorl, 60% fused into base, 3 mm in length, 4 mm in width, broadly elliptic in shape, acute apex, entire margins, outer surface glabrous, inner surface pubescent, color; outer and inner surface when opening and fully open NN155C in color.

*Sepals*.—5, arranged in a single whorl, fused below the apices, average of 0.3 mm in length, 0.5 mm in width at the widest point, acute apex, entire margins, inner and outer surface glabrous, color; inner surface 141A, outer surface flushed with 185A.

*Calyx*.—Funnelform, 1 mm in length and diameter.

*Peduncles*.—Strong, 1 mm in width, glabrous and matte surface, color; young 145A, maturing 145A and flushed with 182A, mature 185A.

*Pedicels*.—None, sessile to peduncle.

Reproductive organs:

*Gynoecium*.—Pistils; 1, average of 3 mm in length, stigma; club-shaped, average of 0.6 mm in width, 143A in color, style; average of 2.5 mm in length, 157A in color, ovary; average of 2 mm in diameter, 143A in color.

*Androecium*.—Stamens; 5, 3.5 mm in length, anthers; flattened, narrow oblong in shape, average of 0.7 mm in width, 0.4 mm in depth, 11C in color, filament 3 mm in length, glossy, 157A in color, surrounded by thin translucent fur-like hairs NN155D in color, pollen; no pollen observed.

*Fruits*.—An average 15 clusters of berries per branch, 7 berries per cluster, fruit size; an average of 1 cm in diameter, 1.3 cm in depth, spherical in shape, smooth in texture, matte surface, color; young fruit 140B, developing fruit 181A, mature fruit; a blend of 77D and N155C.

*Seeds*.—Average of length 3 mm and 2 mm in diameter, 158A in color.

It is claimed:

1. A new and distinct cultivar of *Symphoricarpos* plant named 'Kolmapinpos' as herein illustrated and described.

* * * * *